(12) United States Patent
Maikner

(10) Patent No.: US 6,435,012 B2
(45) Date of Patent: Aug. 20, 2002

(54) METHOD FOR DETERMINATION OF CHROMATOGRAPHIC MEDIA PARAMETERS IN PACKED BEDS OF HYDROPHOBIC POLYMER PARTICLES

(75) Inventor: John Joseph Maikner, Quakertown, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/924,084

(22) Filed: Aug. 7, 2001

Related U.S. Application Data

(60) Provisional application No. 60/245,288, filed on Nov. 2, 2000, and provisional application No. 60/224,373, filed on Aug. 11, 2000.

(51) Int. Cl.[7] ........................ G01N 30/00; G01N 30/90; B01D 15/08
(52) U.S. Cl. .................... 73/61.52; 73/61.63; 210/198.2
(58) Field of Search ................. 73/61.52, 866, 73/61.63, 61.64; 210/198.2, 635, 656; 422/70

(56) References Cited

PUBLICATIONS

E. Meehan, Size Exclusion Chromatography Columns from Polymer Laboratories in *Column Handbook for Size Exclusion Chromatography*, pp 349–366, Academic Press (1999).

*Primary Examiner*—Hezron Williams
*Assistant Examiner*—Jay L. Politzer
(74) *Attorney, Agent, or Firm*—Thomas J. Howell

(57) ABSTRACT

An improved method for measuring the chromatographic properties, such as excluded volume, of hydrophobic polymer substrates is disclosed. Use of 0.05–1 micron sized crosslinked ionically-charged polymer particles, especially emulsion-form or ground polymer particles, as a large-molecule probe, allows environmentally friendly aqueous-based solvent systems to be used as mobile phases to characterize hydrophobic polymer supports for use in analytical or preparative scale chromatographic applications. This method eliminates the use of non-polar organic solvents that is required when conventional non-polar large-molecule probes (such as polystyrene) are used to characterize chromatographic media.

15 Claims, No Drawings

METHOD FOR DETERMINATION OF CHROMATOGRAPHIC MEDIA PARAMETERS IN PACKED BEDS OF HYDROPHOBIC POLYMER PARTICLES

CROSS REFERENCE TO RELATED PATENT APPLICATIONS

This is a non-provisional application of prior pending U.S. provisional application serial number 60/245,288 filed Nov. 2, 2000 and provisional application serial number 60/224,373 filed on August 11, 2000.

BACKGROUND

This invention relates to an improved method for measuring chromatographic media parameters, such as excluded volume and pore volume, of hydrophobic polymer particles in packed beds. Excluded volumes are useful in determining the performance characteristics of hydrophobic polymer substrates (organic or inorganic polymers) used as stationary phases in medium and high pressure reversed phase liquid chromatography (RPC). Chromatographic media properties, such as porosity, compressibility and permeability (flow resistance), are important in selecting polymers for use in high performance chromatographic preparative modes, such as is required in the separation and purification of biomolecules.

Current methods for measuring excluded volumes of chromatographic media in packed beds involves the use of conventional large-molecule "probe" or "marker" materials, such as linear polystyrene or polyethylene glycol. These probe compounds require the use of non-polar mobile phases (such as tetrahydrofuran and toluene) in chromatographic operations; however, the use of non-polar solvents often presents operational problems, such as toxicity, flammability and incompatibility (with aqueous systems). A discussion of performance evaluation (including void-volume determinations) of hydrophobic polymer supports in size-exclusion chromatography is given by E. Meehan, Size Exclusion Chromatography Columns from Polymer Laboratories in *Column Handbook for Size Exclusion Chromatography*, pp 349–366, Academic Press (1999).

The problem addressed by the present invention is to provide an improved method for determining chromatographic media parameters that does not require the use of non-polar solvents and that can be used in aqueous-based solvent systems, for example, water-alcohol mixtures, such as 20% aqueous ethanol.

SUMMARY OF INVENTION

The present invention provides a method for measuring chromatographic media parameters in a packed bed of hydrophobic polymer particles comprising (a) packing a column with hydrophobic polymer particles and a first solvent to provide a packed bed; (b) introducing a large-molecule probe mixture, comprising a crosslinked ionically-charged polymer particle probe and a second solvent, onto the packed bed; (c) eluting the crosslinked ionically-charged polymer particle probe from the packed bed by passing a third solvent through the packed bed, wherein the third solvent is selected from one or more of polar organic solvent and water; and (d) determining an elution volume for the crosslinked ionically-charged polymer particle probe; wherein the chromatographic media parameter is excluded volume, corresponding to the elution volume for the crosslinked ionically-charged polymer particle probe.

In a preferred embodiment, the crosslinked ionically-charged polymer particle probe of the aforementioned method is selected from one or more of anionically-charged emulsion-form polymer particles, cationically-charged emulsion-form polymer particles, anionically-charged ground polymer particles and cationically-charged ground polymer particles, having a particle size from 0.05 to 1 micron.

In another embodiment, the aforementioned method further comprises (i) introducing a small-molecule probe mixture, comprising a small-molecule probe and the second solvent, onto the packed bed; (ii) eluting the small-molecule probe from the packed bed by passing the third solvent through the packed bed; (iii) determining an elution volume for the small-molecule probe; and (iv) determining a pore volume for the hydrophobic polymer particles by subtracting the elution volume for the crosslinked ionically-charged polymer particle probe from the elution volume for the small-molecule probe; wherein the chromatographic media parameter is pore volume.

DETAILED DESCRIPTION

In the determination of the interparticle void volume ("excluded volume") and other chromatographic media performance parameters, we have discovered that the use of a large-molecule probe (or marker) based on crosslinked ionically-charged polymer particles allows for quick and efficient measurements using polar organic solvents and aqueous-based solvent systems that are environmentally friendly. Use of the aforementioned large-molecule probe particles in place of conventional probe materials provides a probe material that (1) is totally excluded from entering the polymer matrix being evaluated, (2) allows the use of polar solvents during the chromatographic process; and (3) does not contribute to hydrophobic interactions between the probe material and the polymer matrix of the packed chromatography column.

In particular, we have discovered that emulsion-form or ground crosslinked polystyrene particles containing ionizable functional groups (such carboxylate, sulfonate or quaternary ammonium chloride) are particularly useful as large-molecule probe materials in the evaluation of various hydrophobic solid media, particularly macroporous polyvinylaromatic polymers, for chromatographic applications. Carboxylate and sulfonate functional groups are representative of "anionically-charged" probe particles and quaternary ammonium functional groups are representative of "cationically-charged" probe particles.

As used throughout the specification, the following terms shall have the designated meanings, unless the context clearly indicates otherwise.

All percentages referred to will be expressed in weight percent (%), based on total weight of polymer or composition involved, unless specified otherwise. The term "(meth)acrylate" or "(meth)acrylic" refers to either the corresponding acrylate or methacrylate derivatives: such as the corresponding acids, esters, amides, substituted esters or substituted amides. The term "copolymer" refers to polymer compositions containing units of two or more different monomers, including positional isomers. The following abbreviations are used herein: g=gram; ppm=parts per million by weight/volume, cm=centimeter, cc=cubic centimeter, mm=millimeter, ml=milliliter, $\mu$m=microns, min=minute. Unless otherwise specified, ranges listed are to be read as inclusive and combinable and temperatures are in degrees centigrade (° C.).

As used herein, chromatographic media parameters include those properties that are typically used to characterize hydrophobic polymer substrates for suitability in specific end use applications, such as the separation and purification of biomolecules using size exclusion chromatography, gel filtration chromatography, gel permeation chromatography, hydrophobic interaction chromatography or reversed phase chromatography. Typical chromatographic media performance parameters of interest to the chromatography practitioner include, for example, compressibility, permeability (flow resistance), % polymer pore volume (% porosity of polymer bed), pore volume, interparticle void volume (% interstitial volume or excluded volume), % polymer solids (volume), polymer porosity (volume pores/volume polymer).

In general, to determine various chromatographic media parameters of polymer substrates, mobile phases (solvents used to transport molecules through the polymer matrix) must be selected for compatibility with the probe molecules such that interactions of the probe molecule with the hydrophobic surface of the polymer particles is minimized and preferably eliminated, otherwise chromatographic performance parameter measurements may be inaccurate and imprecise. Conventional large-molecule probe materials, such as linear polystyrene and polyethylene glycol, may be used for interparticle void volume determinations; however these types of probe materials require the use of nonpolar mobile phases (such as tetrahydrofuran, dichloromethane and toluene) to minimize hydrophobic interactions between the probe material and the polymer surfaces. The probe materials used in the method of the present invention, however, do not require the use of non-polar solvents and can be used in a wide range of polar organic solvents and aqueous-based solvent systems, for example, water or 20% aqueous ethanol, thus eliminating hydrophobic interactions between the probe molecule and the stationary phase (polymer matrix).

In practicing the method of the present invention, small-molecule and large-molecule probe materials may be introduced onto the packed chromatography column containing hydrophobic polymer particles in any manner convenient to obtain the required information on elution times that is needed for determination of chromatographic media parameters. For example, small-molecule and large-molecule probe mixtures may be (a) added onto a packed column concurrently (that is simultaneously), (b) in a staggered fashion (addition of each probe mixture overlapping with the other, with each addition starting and finishing at different times), (c) addition of the large-molecule probe mixture first, followed by addition of the small-molecule probe mixture, or (d) addition of the small-molecule probe mixture first, followed by addition of the large-molecule probe mixture. If characterization of the hydrophobic polymer matrix is desired for excluded volume only, then only the large-molecule mixture need be loaded onto the column and eluted. It will be understood by one skilled in the art of chromatographic separations that selection of addition sequence and flow rates may be varied over a range of conditions in order to obtain the required data.

"Large-molecule" probe materials useful in the method of the present invention include crosslinked ionically-charged polymer particle probes selected from one or more of anionically-charged emulsion-form polymer particles, cationically-charged emulsion-form polymer particles, anionically-charged ground polymer particles and cationically-charged ground polymer particles, having a particle size from 0.05 to 1 $\mu$m. Preferably the particles have a particle size ranging from 0.1 to 0.9, more preferably from 0.1 to 0.5 and most preferably from 0.1 to 0.2 $\mu$m. Suitable crosslinked ionically-charged polymer particles include, for example, crosslinked polystyrene with ionizable functional groups, such as weak-acid functional group (carboxylate group), strong acid functional group (sulfonate) or quaternary ammonium halide functional group. The polystyrene is typically crosslinked with polyvinylaromatic or aliphatic crosslinking monomers. Suitable polyvinylaromatic crosslinkers include, for example, divinylbenzene, trivinylbenzene, divinyltoluene, divinylnaphthalene, divinylanthracene and divinylxylene; preferably the crosslinking monomer is divinylbenzene. Suitable aliphatic crosslinking monomers include, for example, ethylene glycol diacrylate, ethylene glycol dimethacrylate, trimethylolp ropane triacrylate, trimethylolpropane trimethacrylate. The crosslinking monomers are typically used at levels of 1 to 80%, preferably from 1 to 50% and more preferably from 2 to 25%, based on total weight of the emulsion-form or ground crosslinked ionically-charged polymer.

The crosslinked ionically-charged polymers may be used in their various salt forms: ammonium, alkali (such as sodium and potassium) or alkaline earth (such as calcium, magnesium) metal salts; preferably the crosslinked ionically-charged polymers are at least 50% neutralized (salt form), and more preferably at least 75% neutralized. Optionally, the crosslinked ionically-charged polymer, if based on a strong acid such as a sulfonic acid, may be used in its free acid form.

Typical crosslinked anionically-charged polymer probe materials would include, for example, crosslinked polystyrene containing sodium carboxylate, sodium sulfonate or ammonium sulfonate groups; preferably the anionically-charged polymer probe material is crosslinked polystyrene-sulfonate. Additional crosslinked anionically-charged polymer probe materials include, for example, crosslinked poly (meth)acrylic acid in its various salt forms (sodium, potassium or ammonium salts). Additional crosslinked anionically-charged polymer probe materials include, for example, copolymers of styrene or (meth)acrylic acid, where one or more of the following comonomers have been incorporated into the polymer: 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrene sulfonic acid, vinylsulfonic acid, 3-sulfopropyl acrylate, 3-sulfopropyl methacrylate, sulfomethyl acrylamide and sulfomethyl methacrylamide.

Typical crosslinked cationically-charged polymer probe materials include, for example, ammonium salts of crosslinked polyvinylbenzyl chloride; ammonium salts of crosslinked poly(dialkylaminoalkyl(meth)acrylamide) such as poly(3-acrylamidopropyl-trimethylammonium chloride), poly(3-methacrylamidopropyl-trimethylammonium chloride); and ammonium salts of (meth)acrylate esters, such as poly(2-(N,N,N-trimethylammonium chloride)-ethylmethacrylate). By "ammonium" salts, we mean that both quaternary (such as trialkylammonium) and acid (such as dialkylammonium hydrochloride) salts of the amine derivatives may be used.

Suitable "small-molecule" probe materials useful in the method of the present invention include water-soluble inorganic salts (such as, for example, halide, nitrate, sulfate, borate, phosphate salts of ammonium, alkali and alkaline earth metals) and low-molecular weight organic molecules (such as $C_1$–$C_2$ organic acids and salts thereof, $C_1$–$C_3$ alcohols, acetone, toluene and benzene); suitable low-molecular weight organic molecules typically include those having molecular weights below about 200. Typically, the small-molecule probe material is an inorganic salt selected from one or more of sodium chloride, sodium nitrate and calcium chloride.

Solvent systems used in the process of the present invention may vary depending on the purpose or use of the solvent. For example, when packing the column with hydrophobic particles, solvents (designated as first solvent) may include one or more of non-polar organic solvent, polar organic solvent and water, including mixtures of polar organic solvents and water (designated as mixed aqueous-organic solvents). Typical non-polar organic solvents include, for example, tetrahydrofuran, dichloromethane, chloroform, benzene and toluene. Suitable polar organic solvents include those that are water-soluble or watermiscible, such as, for example, $C_1$–$C_3$ alcohols (methanol, ethanol, n-propanol and isopropanol), $C_1$–$C_2$ organic acids (formic acid, acetic acid), $C_3$–$C_4$ ketones (acetone, methylethyl ketone) and acetonitrile. Preferably, the polar organic solvents are selected from one or more of methanol, ethanol, n-propanol and isopropanol. Typical mixed aqueous-organic solvents include for example, 2 to 99% polar organic solvent in water, preferably 5 to 50%, and more preferably 10 to 30% polar organic solvent, such as $C_1$–$C_3$ alcohol. Preferably, the first solvent is an aqueous-based solvent, that is, water or a mixed aqueous-organic solvent.

When introducing large-molecule or small-molecule probe mixtures onto the packed bed, solvents (designated as second solvent) used to make up the probe mixtures may include any of the solvent systems described above as first solvents. Preferably, the second solvent is an aqueous-based solvent, that is, water or a mixed aqueous-organic solvent.

When eluting the large-molecule or small-molecule probe from the packed bed, solvents used for elution (designated as third solvent) comprise one or more of polar organic solvent and water, including mixed aqueous-organic solvents, as described above. Preferably, the third solvent is an aqueous-based solvent, that is, water or a mixed aqueous-organic solvent.

Typically, the first and second solvents used in the process of the present invention are the same as the third solvent as a matter of convenience; however, each solvent system may be selected independently of the other.

As described above, suitable aqueous-based solvents include water solutions and mixed aqueous-organic solvent systems. Preferably, the aqueousbased solvent is a mixed aqueous-organic solvent system since the presence of some polar organic solvent provides improved wettability of the hydrophobic polymer particles during packing and operation of the chromatography column.

Concentrations of polar organic solvent in the mixed aqueous-organic solvent mixtures may vary, depending on the type of small-molecule probe used in characterization of the chromatographic media. For example, when low-molecular weight organic molecules are used as small-molecule probes, from 75–100% polar organic solvent may be used to elute the small-molecule probe from the packed column. When inorganic salts are used as small-molecule probes, typically from zero (that is, 100% water) up to 75%, preferably from 5 to 50% and more preferably from 10 to 30% polar organic solvent, based on total weight of the mixed aqueous-organic solvent, may be used to elute the small-molecule probe.

When the aqueous-based solvent system is water, that is, contains little or no organic solvent, the solvent system may optionally contain water-soluble salts, such as buffer agents, for example, phosphate, carbonate, bicarbonate, borate and acetate salts. When used, these salts are typically present at levels from 50 ppm to 5%, and preferably from 1000 ppm to 1%, in the aqueous-based solvent system.

Suitable detection methods useful for detecting the presence of the probe materials in the effluents of the chromatography columns include, for example, UV spectrophotometry, infrared spectrophotometry, conductivity and refractive index techniques. The particular detection method selected will depend on the type of probe particle being detected and may be any detection method sufficient to sense the small-molecule or large-molecule probe. For detection of the inorganic salt probes, conductivity and refractive index methods are preferred. For detection of the crosslinked ionically-charged polymer particle probes, UV spectrophotometry, refractive index or conductivity methods are preferred.

A chromatography column packed with polymeric particles may be visualized as having four different types of "volumes."

The liquid volume between the particles of the stationary phase (polymer beads or polymer matrix) is known as the interstitial volume, interparticle void volume, void volume or excluded volume ($V_o$).

The liquid volume within the pores of the stationary phase is the pore volume ($V_i$).

The volume of the solid portion of the stationary phase is the polymer skeletal volume ($V_g$).

The total volume of the packed bed ($V_t$) corresponds to the sum of the above volumes: $V_t = V_o + V_i + V_g$.

All molecules, regardless of size, have access to $V_o$ and none of the molecules have access to $V_g$. Access to $V_i$ depends on the size of the molecules and the size of the pores in the polymer matrix. Large molecules (for example, molecular weights larger than about 20,000 daltons) generally cannot penetrate the pores of the polymer matrix due to pore size limitations (such as where average pore sizes are typically less than about 100 Angstrom units) and the accessible volume for large molecules is typically equal to $V_o$. Medium-size molecules (for example, molecular weights of 2,000 to 10,000 daltons) may partially penetrate the pore structure and the "apparent" volume (elution volume) will be equal to $V_o$ plus the part of $V_i$ that is accessible to medium-size molecules. Small molecules (such as those having molelcular weights less than about 1,000 daltons) typically have complete access to the polymer matrix and the corresponding elution volume will be equal to $V_o + V_i$. Molecules passing through the column will exit in order of their accessible volumes (or "apparent" volumes), and the latter are measured as the corresponding elution volumes The largest molecules (for example, the large-molecule probe) will elute first with a volume equal to $V_o$ and the smallest molecule (for example, inorganic salt or small-molecule probe) will elute last with a volume equal to $V_o + V_i$.

The choice of an appropriate hydrophobic polymer matrix for chromatographic purposes depends on the molecular size and the chemical properties of the substances to be separated. Most polymer matrices will fractionate (separate) target molecules within a particular molecular weight range, depending on the pore size distribution in the hydrophobic polymer particles. The function of the hydrophobic polymer matrix is to provide a continuous decrease in accessibility for the targeted molecules (for example, biomolecules) of increasing size where the largest molecules are eluted from a chromatographic column first and the smallest are eluted last.

Among the hydrophobic solid media useful as substrates for chromatographic applications are, for example:

(a) hydrophobically-modified silica-based polymers, such as those based on silica particles that have been surface treated with trimethylsilyl groups, $(C_8-C_{20})$alkyl groups or other hydrophobic groups;

(b) polyvinylaromatic polymers, such as crosslinked polystyrene and polydivinylbenzene copolymers;

(c) poly(meth)acrylate or acrylic-based copolymers, such as alkyl(meth)acrylate copolymers and trimethylolpropane tri(meth)acrylate copolymers.

By "hydrophobic" we mean polymers that are substantially non-polar in nature, that is, they contain little or no polar, ionizable or hydrogen-bonding functionality (the latter are typically characteristic of hydrophilic characteristics). For the purposes of the present invention, hydrophobic polymers also include hydrophilic polymer substrates that have had their surfaces hydrophobically-modified, such as silica or other hydrophilic substrates whose surfaces have been chemically modified or coated with hydrophobic (water-insoluble) functionality (such as fluorocarbon or alkyl groups).

Hydrophobic polymer particles selected as stationary phases for chromatography applications are typically based on polymers selected from one or more of organic copolymer and hydrophobically-modified inorganic polymer. Preferably, the organic copolymer is selected from one or more of polyvinylaromatic copolymer and poly(meth)acrylate copolymer. When hydrophobically-modified inorganic polymers are used, the hydrophobic polymers are typically selected from one or more of silica-based, alumina-based and zeolite-based polymer.

Hydrophobic polymers useful for the separation and purification of biomolecules via high performance reverse phase liquid chromatography (such as in columns from 2 to 100 cm in diameter) typically have average particle size diameters from 2 to 150 µm. Hydrophobic polymers useful for the separation and isolation of biomolecules via large scale adsorption processes (such as in columns up to several meters in diameter or in fermentation broths) typically have average particle size diameters from 150 up to 600 µm. Preferably, the hydrophobic polymers are spherical copolymer beads having particle diameters from 2 to 150 µm, more preferably from 5 to 100 µm and most preferably from 10 to 75 µm. Particularly preferred are macroporous polymers that are produced by suspension polymerization and possess surface areas from 200 to 1500 square meters per gram ($m^2$/g) and preferably from 300 to 1200 $m^2$/g. The macroporous polymers are preferably those of the type described in U.S. Pat. No. 4,382,124, for example, in which porosity is introduced into the copolymer beads by suspension-polymerization in the presence of a porogen (also known as "phase extender" or "precipitant"), that is, a solvent for the monomer but a non-solvent for the polymer. Conventional macroporous polymers, such as those prepared according to U.S. Pat. No. 4,382,124, typically encompass the use of a wide range of porogen types, porogen concentrations relative to the monomer phase, monomer types, crosslinking monomer types, crosslinker levels, polymerization initiators and initiator concentrations.

Polyvinylaromatic monomers that may be used in the preparation of macroporous polymers suitable for use in chromatographic separations include, for example, divinylbenzene, trivinylbenzene, divinyltoluene, divinylnaphthalene, divinylanthracene and divinylxylene; preferably the polyvinylaromatic monomer is divinylbenzene. Suitable macroporous polymers typically comprise 50 to 100% and preferably 75 to 90% polyvinylaromatic monomer units.

Monounsaturated vinylaromatic monomers that may be used in the preparation of macroporous copolymers suitable for use in chromatographic separations include, for example, styrene, α-methylstyrene, $(C_1-C_4)$alkylsubstituted styrenes, halo-substituted styrenes (such as dibromo- and tribromostyrene), vinylnaphthalene and vinylanthracene; preferably the monounsaturated vinylaromatic monomer is selected from one or more of styrene and $(C_1-C_4)$alkyl-substituted styrenes. Included among the suitable $(C_1-C_4)$ alkyl-substituted styrenes are, for example, ethylvinylbenzenes, vinyltoluenes, diethylstyrenes, ethylmethylstyrenes and dimethylstyrenes; preferably the monounsaturated vinylaromatic monomer is ethylvinylbenzene. Typically, suitable macroporous polymers comprise zero to 50% and preferably 10 to 25% monounsaturated vinylaromatic monomer units.

Preferred macroporous polymers useful for chromatographic separations include divinylbenzene copolymer, styrene-divinylbenzene copolymer, divinylbenzene-ethylvinylbenzene copolymer and styrene-ethylvinylbenzene-divinylbenzene copolymer. Most preferable are macroporous divinylbenzene-ethylvinylbenzene and styrene-ethylvinylbenzene-divinylbenzene copolymers. These macroporous polymers are especially useful in packed chromatography column applications where porosity and mechanical strength of the polymer allows for high performance separation and purification of biomolecules at high throughput rates without pressure buildup on prolonged use.

Acrylic-based monomers that may be used in the preparation of suitable hydrophobic polymer substrates include, for example, $(C_1-C_{20})$alkyl (meth)acrylates. In addition, the alkyl (meth)acrylate monomers may be copolymerized with functionalized (meth)acrylate derivatives, such as hydroxyalkyl (meth)acrylates, amides of ethylenically unsaturated $(C_3-C_6)$carboxylic acids that are substituted at the nitrogen by one or two $(C_1-C_4)$alkyl groups, dimethylaminopropyl (meth)acrylamide and 2-(dimethylamino)ethyl(meth) acrylate. When used as comonomers, the functionalized (meth)acrylate derivatives typically comprise up to 50% and preferably less than 20%, based on total weight of the polymer.

Among the chromatographic media parameters of interest to the chromatography practitioner are "permeability" or "flow resistance" properties. The permeability (K) is related to the backpressure generated in a column through Darcy's Law (Equation 1):

$$\Delta P = \mu V / [K(d_p)^2] \qquad \text{Equation 1}$$

where:

µ=viscosity (milliPascal·second or centipoise)
V=linear velocity (cm/hr)
ΔP=pressure drop (bars)
$d_p$=mean particle size of the polymer (microns)

The units of the above variables are expressed in their common form; it is understood that unit conversion is required to render Equation 1 dimensionless. Under laminar flow conditions, which are typical for chromatographic separation and purification applications, the backpressure in a column can also be expressed by the Carman-Kozeny Equation (Equation 2):

$$\Delta P = 150 \cdot [(1-\epsilon)^2/\epsilon^3] \mu V/(d_p)^2 \quad \text{Equation 2}$$

where:

$\epsilon$=interparticle void volume (cc/cc)

References, such as *Fundamentals of Preparative and Nonlinear Chromatography*, G. Guiochon, S. Goshan Shirazi and A. Katti; Academic Press (1994) and *Unit Operations in Chemical Engineering*, W. L. McCabe, J. C. Smith and P. Harriott; McGraw Hill (1985), may be consulted for further general and specific details on Darcy's Law and the Carman-Kozeny Equation (Equations 1 and 2).

By combining Equations 1 and 2, it can be seen that permeability (or flow resistance) in the chromatography column is related to the interparticle void volume of the polymer resin bed (that is, the volume between polymer particles); $\epsilon$ is expressed as volume of voids per unit volume of polymer bed in this case. This relationship is expressed by Equation 3:

$$1/K = 150 \cdot [(1-\epsilon)^2/\epsilon^3] \quad \text{Equation 3}$$

The characteristic "flow resistance" value of a polymer (inverse of the permeability) is an indication of how well the polymer will perform under medium to high pressure conditions: low flow resistance values represent low compressibility and high flow resistance values represent poor compressibility.

Some embodiments of the invention are described in detail in the following Example. All ratios, parts and percentages are expressed by weight unless otherwise specified, and all reagents used are of good commercial quality unless otherwise specified. Abbreviations used in the Examples and Tables are listed below with the corresponding descriptions:

v/v=volume/volume w/v=weight/volume nm=nanometer

EXAMPLE 1

This example describes how polyvinylaromatic macroporous polymers were evaluated for their permeability characteristics, that is, resistance to compression. In order for the polymers to be characterized by their "flow resistance" or 1/K values (see Equation 3), accurate determinations of void volumes were needed. In this case, the polymer tested was a polymer of 80% divinylbenzene and 20% ethylvinylbenzene, having a porosity of 1.9 cc/g, pore volume of 0.67 cc/cc, surface area of 947 m$^2$/g and an average particle size of about 30 $\mu$m.

In industrial high pressure liquid chromatography, columns are equipped with a piston that exerts a force (pressure) directly onto the resin. It is preferred to keep the piston actively compressing the bed at a pressure that is equal to or greater than the maximum anticipated flow pressure throughout the chromatographic cycle. In order to test the permeability characteristics of the polymers, polymer resin was packed into a ProChrom™ Dynamic Axial Compression column (Model LC.50) and compressed with the piston set first at 10 and then at 60 bar compression pressure. A detailed description follows:

Approximately 100 g of dry polymer resin (corresponding to approximately 500 ml wet resin) was added to 700 ml of a solution of 20% ethanol/water (v/v) and allowed to stand at ambient temperature for at least 2 hours. This polymer sample was agitated into slurry form and poured into a 5 cm (internal diameter)×54 cm (length) Prochrom™ Dynamic Axial Compression L.C.50 316 L stainless steel column (manufactured by Prochrom S.A., France). A piston assembly (driven by external air pressure converted into hydraulic oil pressure) was activated to apply a variable pressure to the polymer resin bed. The piston was first set to deliver approximately 10 bar of hydraulic pressure and the resin bed was considered packed when the piston no longer moved. The height of the bed was then measured at 21.5 cm, corresponding to a total packed bed volume of 421.9 cc wet polymer ($=V_t=V_o+V_i+V_g$). A flow of 10 ml/min of a solution of 20% ethanol/water (v/v) was passed through the resin bed for 30 minutes to equilibrate the bed.

To determine the total volume of voids in the packed bed (sum of intraparticle ($V_i$) and interparticle ($V_o$) voids), 2 ml of 1% sodium chloride (w/v in 20% aqueous ethanol), corresponding to the small-molecule probe mixture, was injected into the system (flowing at 10 ml/min). The sodium chloride (small-molecule probe) was detected by a conductivity detector; elution time for the sodium chloride was 31.1 minutes, which corresponded to an elution volume of 311 ml [$=V_{sm}$].

To determine the interparticle (interstitial or excluded) void volume only ($V_o$), a solution of 20% ethanol (aqueous) containing 1% (w/v) of a 0.1–0.9 $\mu$m crosslinked sulfonated polystyrene (emulsion-form or ground) particles, corresponding to the large-molecule probe mixture, was injected into the stream of 20% ethanol (aqueous) flowing through the bed at 10 ml/min. The large-molecule probe were detected by UV spectrophotometer, set at 280 nm. The elution time for the large-molecule probe was 13.7 minutes, which corresponded to an elution volume of 137 ml [$=V_{lm}$].

The calculated volume [$V_g$] of polymer solids was:

$$[V_t - V_{sm}] = 421.9 - 311 = 110.9 \text{ cc.}$$

The calculated volume [$V_t$] of polymer pores was: [$V_{sm} - V_{lm}$]=174 cc.

The calculated volume [$V_o$] of interstitial voids (excluded volume) was:

$$[V_t - V_i - V_g] = V_{lm} = 137 \text{ cc.}$$

Calculated % polymer solids volume=$V_g/V_t$=110.9/421.9=26.3%

Calculated % polymer pore volume (% porosity)=$V_i/V_t$=174/421.9=41.2%

Calculated % interstitial volume (% void volume)=$V_o/V_t$=174/421.9=32.5%

Calculated porosity of polymer=$V_i/(V_i+V_g)$=174/(174+110.9)=0.61 cc/cc

The above process was repeated again at 60 bar pressure, with the following results:

The height of the bed (60 bar) was measured at 17.0 cm, corresponding to a total packed bed volume of 333.6 cc wet polymer [$=V_t$].

The elution time for the sodium chloride was 22.3 minutes, which corresponded to an elution volume of 223 ml [$=V_{sm}$].

The elution time for the large-molecule probe was 7.4 minutes, which corresponded to an elution volume of 74 ml [$=V_{lm}$].

The calculated volume [$V_g$] of polymer solids was:

$$[V_t - V_{sm}] = 333.6 - 223 = 110.6 \text{ cc.}$$

The calculated volume [$V_i$] of polymer pores was:

$$[V_{sm} - V_{lm}] = 149 \text{ cc.}$$

The calculated volume [$V_o$] of interstitial voids (excluded volume) was:

$[V_t-V_i-V_g]=V_{lm}=74$ cc.

Calculated % polymer solids volume=$V_g/V_t$=110.6/333.6= 33.2%

Calculated % polymer pore volume (% porosity)=$V_i/V_t$= 149/333.6=44.7%

Calculated % interstitial volume (% void volume)=$V_o/V_t$= 74/333.6=22.2%

Calculated porosity of polymer=$V_i/(V_i+V_g)$=149/(149+ 110.6)=0.57 cc/cc

The various chromatographic polymer properties measured above may be used to determine the value of "ϵ" that is needed for calculations based on Equations 2 and 3. It is important to generate accurate and precise values for $V_o$ and $V_i$ in order to provide reliable permeability and compressibility characteristics of polymer supports used in chromatographic separations. As would be recognized by the skilled chromatography practitioner, the volumes referred to ($V_t$, $V_o$, $V_i$ and $V_g$) are independent of and exclusive of other components of the "total chromatographic column system" volume, that is: "dead" volumes, transfer line volumes and column head volumes—the latter are taken into account during measurement of the chromatographic media parameters.

What is claimed is:

1. A method for measuring chromatographic media parameters in a packed bed of hydrophobic polymer particles comprising:
   (a) packing a column with hydrophobic polymer particles and a first solvent to provide a packed bed;
   (b) introducing a large-molecule probe mixture, comprising a crosslinked ionically-charged polymer particle probe and a second solvent, onto the packed bed;
   (c) eluting the crosslinked ionically-charged polymer particle probe from the packed bed by passing a third solvent through the packed bed, wherein the third solvent is selected from one or more of polar organic solvent and water; and
   (d) determining an elution volume for the crosslinked ionically-charged polymer particle probe; wherein the chromatographic media parameter is excluded volume, corresponding to the elution volume for the crosslinked ionically-charged polymer particle probe.

2. The method of claim 1 further comprising:
   (i) introducing a small-molecule probe mixture, comprising a small-molecule probe and the second solvent, onto the packed bed;
   (ii) eluting the small-molecule probe from the packed bed by passing the third solvent through the packed bed;
   (iii) determining an elution volume for the small-molecule probe; and
   (iv) determining a pore volume for the hydrophobic polymer particles by subtracting the elution volume for the crosslinked ionically-charged polymer particle probe from the elution volume for the small-molecule probe;

wherein the chromatographic media parameter is pore volume.

3. The method of claim 1 wherein the hydrophobic polymer particles are selected from one or more of organic copolymer and hydrophobically-modified inorganic polymer.

4. The method of claim 1 wherein the first solvent is selected from one or more of non-polar organic solvent, polar organic solvent and water.

5. The method of claim 1 wherein the second solvent is selected from one or more of non-polar organic solvent, polar organic solvent and water.

6. The method of claim 1 wherein the third solvent is a mixed aqueousorganic solvent comprising from 2 to 99% polar organic solvent, based on total weight of the mixed aqueous-organic solvent.

7. The method of claim 1 wherein the crosslinked ionically-charged polymer particle probe is selected from one or more of anionically-charged emulsion-form polymer particles, cationically-charged emulsion-form polymer particles, anionically-charged ground polymer particles and cationically-charged ground polymer particles, having a particle size from 0.05 to 1 micron.

8. The method of claim 1 wherein the crosslinked ionically-charged polymer particle probe is crosslinked polystyrenesulfonate.

9. The method of claim 2 wherein the small-molecule probe is selected from one or more of inorganic salt and low-molecular weight organic compound.

10. The method of claim 9 wherein the inorganic salt is selected from one or more of sodium chloride, sodium nitrate and calcium chloride.

11. The method of claim 1 wherein the crosslinked ionically-charged polymer particle probe is crosslinked trimethylammonium polyvinylbenzyl chloride.

12. The method of claim 3 wherein the organic copolymer is selected from one or more of polyvinylaromatic copolymer and poly(meth)acrylate copolymer.

13. The method of claim 3 wherein the hydrophobically-modified inorganic polymer is selected from one or more of silica-based and zeolite-based polymer.

14. The method of claim 3 wherein the organic copolymer is selected from one or more of divinylbenzene-ethylvinylbenzene copolymer and styrene-ethylvinylbenzene-divinylbenzene copolymer.

15. The method of claim 6 wherein the polar organic solvent is selected from one or more of methanol, ethanol, n-propanol and isopropanol.

* * * * *